United States Patent [19]

Kaihoh et al.

[11] Patent Number: 5,430,028
[45] Date of Patent: Jul. 4, 1995

[54] 5-AMINOQUINOLONE CARBOXYLIC ACID DERIVATIVE AND ANTIBACTERIAL AGENT CONTAINING THE SAME AS ACTIVE INGREDIENT

[75] Inventors: Terumitsu Kaihoh, Chiba; Sunao Takeda, Ichihara; Fujiko Konno, Chiba; Akihiro Shibata, Yachiyo; Masaru Matsumoto, Tomisatomachi; Takemitsu Asaoka, Narita; Hideaki Matsuda, Abiko; Tadayuki Kuraishi, Narashino, all of Japan

[73] Assignee: SS Pharmaceutical Co., Ltd., Tokyo, Japan

[21] Appl. No.: 185,898

[22] PCT Filed: May 25, 1993

[86] PCT No.: PCT/JP93/00694
§ 371 Date: Jan. 26, 1994
§ 102(e) Date: Jan. 26, 1994

[87] PCT Pub. No.: WO93/24460
PCT Pub. Date: Dec. 9, 1993

[30] Foreign Application Priority Data

May 26, 1992 [JP] Japan ................... 4-133394

[51] Int. Cl.⁶ ............... A61K 31/55; A61K 31/505; C07D 243/08; C07D 243/00
[52] U.S. Cl. ................... 514/212; 514/213; 540/492; 540/575; 540/597
[58] Field of Search ............ 514/212, 213; 540/492, 540/575, 597

[56] References Cited

U.S. PATENT DOCUMENTS 4,795,751 1/1989 Matsumoto et al. ............ 514/254
4,894,458 1/1990 Masuzawa et al. ............ 546/156

FOREIGN PATENT DOCUMENTS 62-215572 9/1987 Japan.
62-277362 12/1987 Japan.
63-275567 11/1988 Japan.

*Primary Examiner*—Mukund J. Shah
*Assistant Examiner*—Matthew V. Grumbling
*Attorney, Agent, or Firm*—Oblon, Spivak, McClelland, Maier, & Neustadt

[57] ABSTRACT

A 5-aminoquinolone carboxylic acid derivative represented by the following general formula (1):

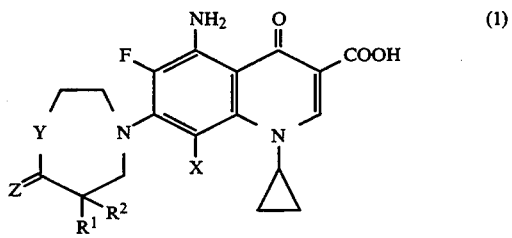

wherein $R^1$ means a hydrogen atom, an amino group, a linear or branched alkyl group having 1-5 carbon atoms and an alkylamino group containing a linear or branched alkyl group having 1-5 carbon atoms, $R^2$ denotes a hydrogen atom or a linear or branched alkyl group having 1-5 carbon atoms, X stands for a halogen atom, Y means $CH_2$, NH, $CHR^3$ $NR^3$, ($R^3$ denoting a linear or branched alkyl group having 1-5 carbon atoms) or an oxygen atom, and Z stands for an oxygen atom or 2 hydrogen atoms, or a salt thereof, and an antibacterial agent containing such a derivative or salt as an active ingredient.

The derivative or salt thereof exhibits strong anti-bacterial activities against Grampositive bacteria including tolerant bacteria, and is satisfactorily absorbed in a living body.

2 Claims, No Drawings

5-AMINOQUINOLONE CARBOXYLIC ACID DERIVATIVE AND ANTIBACTERIAL AGENT CONTAINING THE SAME AS ACTIVE INGREDIENT

This application is a Rule 37 CFR 1.371 of PCT/JP93/00694 filed May 25, 1993.

TECHNICAL FIELD

The present invention relates to a novel 5-aminoquinolone carboxylic acid derivative or a salt thereof, which has an excellent antibacterial activity against Gram-negative bacteria including tolerant bacteria, and Gram-positive bacteria, and an antibacterial agent containing such a derivative or salt as an active ingredient.

BACKGROUND ART

Synthetic antibacterial agents such as nalidixic acid and piromidic acid have heretofore been known as therapeutic agents for infective diseases. However, these agents have involved a drawback that they exhibit insufficient effect on intractable diseases such as pyocyanic infection.

Meanwhile, quinolone carboxylic acid derivatives substituted with a fluorine atom at 6 position, such as norfloxacin, ofloxacin, cyprofloxacin and sparfloxacin have been developed and widely used clinically because of their strong antibacterial activities against Gram-negative bacteria.

However, the conventional synthetic antibacterial agents have involved drawbacks in low bioavailability because of their poor absorptivity in a living body, and in low antibacterial activity against Gram-positive bacteria, in particular, tolerant bacteria such as methicillin-resistant *Staphylococcus aureus*.

Therefore, it is an object of the present invention to provide an antibacterial agent which has strong antibacterial activities against both Gram-negative bacteria and Gram-positive bacteria including tolerant bacteria, and also has superior absorptivity.

In view of the foregoing circumstances, the present inventor has synthesized a great number of quinolone derivatives to investigate their antibacterial activities and absorptivity into the living body. As a result, it has been found that 5-aminoquinolone carboxylic acid derivatives represented by the general formula (1), which will be described subsequently, and salts thereof exhibit extremely enhanced antibacterial activities against Gram-positive bacteria, in particular, tolerant bacteria thereof compared with that of the conventional quinolone carboxylic acid derivatives while retaining good antibacterial activities against Gram-negative bacteria, and also have excellent absorptivity, leading to completion of the present invention.

DISCLOSURE OF THE INVENTION

The present invention is directed to a 5-aminoquinolone carboxylic acid derivative represented by the following general formula (1):

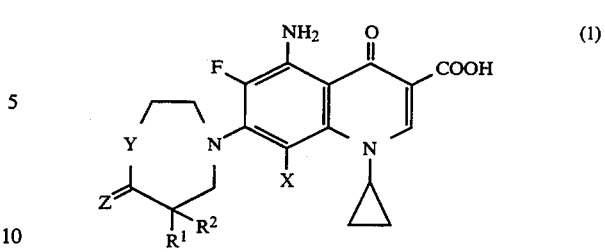

wherein $R^1$ means a hydrogen atom, an amino group, a linear or branched alkyl group having 1–5 carbon atoms and an alkylamino group containing a linear or branched alkyl group having 1–5 carbon atoms, $R^2$ denotes a hydrogen atom or a linear or branched alkyl group having 1–5 carbon atoms, X stands for a halogen atom, Y means $CH_2$, NH, $CHR^3$ $NR^3$ ($R^3$ denoting a linear or branched alkyl group having 1–5 carbon atoms) or an oxygen atom, and Z stands for an oxygen atom or two hydrogen atoms, or a salt thereof, and an antibacterial agent containing such a derivative or salt as an active ingredient.

BEST MODE FOR CARRYING OUT THE INVENTION

The 5-aminoquinolone carboxylic acid derivative according to the present invention is represented by the general formula (1). In the formula, examples of the linear or branched alkyl group having 1–5 carbon atoms include methyl, ethyl, n-propyl, isopropyl, n-butyl, isobutyl, tert-butyl and n-pentyl.

Examples of the salt of the compound (1) according to the present invention include alkali metal salts, inorganic acid salts and organic acid salts. More specifically, the alkali metal salts include lithium, sodium and potassium salts, and the like. The inorganic acid salts include hydrochlorides, sulfates, nitrates, hydrobromides, phosphates and the like. The organic acid salts include acetates, fumarates, maleates, lactates, succinates, citrates, malates, oxalates, methanesulfonates, benzenesulfonates, p-toluenesulfonates and the like.

The compound (1) of the present invention can be prepared by reacting a compound (3) with a compound (2) in accordance with, for example, the following reaction scheme:

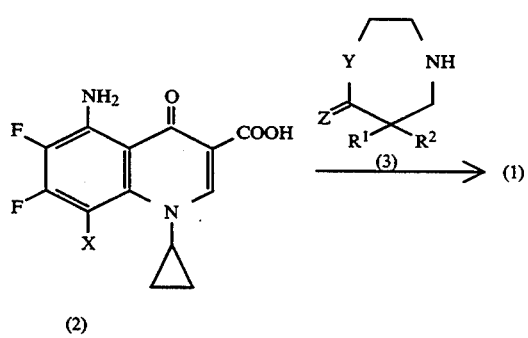

wherein $R^1$, $R^2$, X, Y and Z each have the same meaning as defined above.

The starting compound (2) used in the above-described process is a known compound, and can be prepared in accordance with, for example, a process described in Japanese Patent Application Laid-Open No. 201869/1987 or 187459/1987. The compound (3) can also be prepared in accordance with a known process, for example, a process described in Journal of American Chemical Society, 106, 630 (1984).

In order to prepare the compound (1) of the present invention from the compounds (2) and (3), it is only necessary to use the compound (3) in an amount of 1–5 moles per mole of the compound (2) to react them for 1–10 hours at room temperature or under reflux in a solvent such as acetonitrile, dimethyl sulfoxide, dimethylformamide, hexa-methylphosphoric triamide, pyridine or 1-methyl-2-pyrrolidone. After completion of the reaction, a crude product is obtained by filtration of the resulting precipitate or evaporation of solvent. The thus-obtained crude product is purified by silica gel column chromatography or recrystallization, thereby obtaining the compound (1) of the present invention as a pure product.

The thus-obtained compound (1) according to the present invention can be converted into salts, for example, such alkali metal salts, inorganic acid salts and organic acid salts as described above by a method known per se in the art, as needed.

When the compound (1) thus obtained is used as an antibacterial agent, the dose thereof varies according to the weight, age, sex, dosing method, physical condition and diseased condition of the patient to be dosed, and the like. However, it is preferably dosed in an amount of about 100–800 mg/day for oral administration or about 5–40 mg/day for parenteral administration.

The compound (1) according to the present invention can be used to prepare antibacterial agents in various forms such as tablets, granules, powders, capsules, suspensions, injections and suppositories in accordance with usual methods. In order to produce a solid preparation, it is preferable to add an excipients, and optionally a binder, disintegrator, lubricant, colorant, flavor, extender, coating, sugar coating and/or the like to the compound (1) and then form the resultant mixture into tablets, granules, powder, capsules, suppository or the like. In the case where an injection is prepared, it is only necessary to dissolve, disperse or emulsify the compound (1) in an aqueous vehicle of water for injection or to prepare powder for injection so as to dissolve it in water for injection when used. Administration methods of the injection include intravenous administration, intra-arterial administration, intraportal administration, intra-peritoneal administration, intramuscular administration and subcutaneous administration.

EXAMPLES

The present invention will hereinafter be described in more detail by the following examples and a test example. However, it should be borne in mind that this invention is not limited to and by these examples only.

Example 1

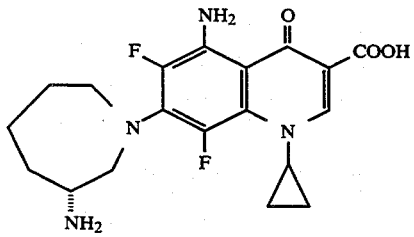

(R)-5-Amino-7-(3-amino-2,3,4,5,6,7-hexahydro-1H-azepin-1-yl)-1-cyclopropyl-6,8-difluoro-1,4-dihydro-4-oxoquinoline-3-carboxylic acid (Compound No. 1-1):

A suspension of 100 mg (0.34 mmol) of 5-amino-1-cyclopropyl-6,7,8-trifluoro-1,4-dihydro-4-oxoquinoline-3-carboxylic acid (2-1) and 114 mg (1.0 mmol) of (R)-3-amino-hexahydro-1H-azepin in acetonitrile was refluxed for 3 hours. After the suspension was allowed to cool, a precipitate was collected by filtration. The resultant crude product was recrystallized from a mixed solvent of chloroform and ethanol to obtain 52 mg (yield: 39%) of the intended compound (1-1) according to the present invention. Pale yellow powder (CHCl$_3$-EtOH); m.p.: 235°–238° C. (decomposed); IR (KBr): 3475, 2940, 1630 cm$^{-1}$; $^1$H-NMR (D$_2$O+NaOD) δ: 0.65–1.89(10H,m), 2.83–3.48(5H,m), 3.68(1H,m), 8.27(1H,s).

Example 2

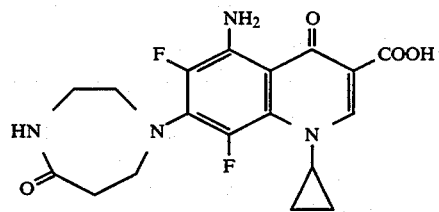

5-Amino-1-cyclopropyl-6,8-difluoro-7-(2,3,4,5,6,7-hexahydro-1H-1,4-diazepin-5-on-1-yl)-1,4-dihydro-4-oxo-quinoline-3-carboxylic acid (Compound No. 1-2):

A suspension (2 ml) of 100 mg (0.34 mmol) of the compound (2-1) and 114 mg (1.0 mmol) of 2,3,4,5,6,7-hexahydro-1H-1,4-diazepin-5-on in hexamethylphosphoric triamide (HMPA) was heated for 4 hours at 100° C. on an oil bath. The resultant product was subjected to sucking filtration, washed with ether, and then crystallized from a mixed solvent of chloroform and ethanol to obtain 68 mg (yield: 51%) of the intended compound (1-2) according to the present invention.

Yellow needles (CHCl$_3$-EtOH) m.p.: >300° C.; IR (KBr): 3410, 1725, 1630 cm$^{-1}$; $^1$H-NMR (DMSO-d$_6$) δ: 0.98–1.13(4H,m), 2.55–2.74(2H,m), 3.25–3.52(7H,m), 4.02(1H,m), 7.27(2H,brs), 7.71(1H,brs), 8.51(1H,s).

Example 3

The following compounds (Compound Nos. 1-3 through 1-8) were obtained by reactions similar to Example 1 or 2.

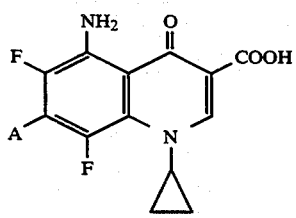

Compound No. (1-3):
5-Amino-1-cyclopropyl-6,8-difluoro-7-(2,3,4,5,6,7-hexahydro-1H-azepin-1-yl)-1,4-dihydro-4-oxoquinoline-3-carboxylic acid:

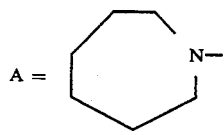

Yellow plates (CHCl₃-EtOH) m.p.: 234°–236° C.; IR (KBr): 3455, 2940, 1710, 1635 cm⁻¹; ¹H-NMR (CDCl₃) δ: 0.90–1.25(4H,m), 1.50–1.90(5H,m), 3.35–3.58(4H,m), 3.92(1H,m), 4.90(2H,brs), 8.62(1H,s).
Compound No. (1-4):
5-Amino-1-cyclopropyl-6,8-difluoro-7-(3,3,5-trimethyl-2,3,4,5,6,7-hexahydro-1H-azepin-1-yl)-1,4-dihydro-4-oxo-quinoline-3-carboxylic acid:

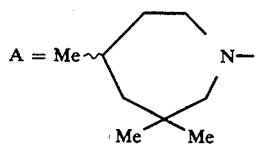

Yellow plates (Et₂O-n-hexane); m.p.: 148.5°–150° C.; IR (KBr): 3450, 2950, 1715, 1630 cm⁻¹; ¹H-NMR (CDCl₃) δ: 0.79–1.43(15H,m), 1.62–1.80(2H,m), 2.09(1H,br), 3.12–3.53(4H,m), 3.93(1H,m), 5.17(2H,brs), 8.63(1H,s).
Compound No. (1–5):
(S)-5-Amino-7-(3-amino-2,3,4,5,6,7-hexahydro-1H-azepin-1-yl)-1-cyclopropyl-6,8-difluoro-1,4-dihydro-4-oxoquinoline-3-carboxylic acid:

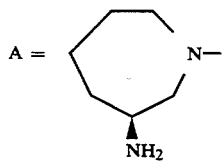

Pale yellow powder (CHCl₃-EtOH) m.p.: 249–252° C. (decomposed); IR (KBr): 3475, 2940, 1635 cm⁻¹; ¹H-NMR (D₂O+NaOD) δ: 0.62–1.91(10H,m), 2.75–3.45(5H,m), 3.66(1H,m), 8.31(1H,s).
Compound No. (1-6):
5-Amino-7-(3-amino-2,3,4,5,6,7-hexahydro-1H-azepin-1-yl)-1-cyclopropyl-6,8-difluoro-1,4-dihydro-4-oxoquinoline-3-carboxylic acid:

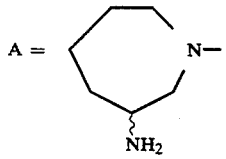

Pale yellow powder (CHCl₃-EtOH) m.p.: 245°–248° C. (decomposed); IR (KBr): 3475, 2940, 1635 cm⁻¹; ¹H-NMR (D₂O+NaOD) δ: 0.70–1.84(10H,m), 2.80–3.48(5H,m), 3.70(1H,m), 8.28(1H,s).
Compound No. (1-7):
5-Amino-1-cyclopropyl-6,8-difluoro-7-(4-ethyl-2,3,4,5,6,7-hexahydro-1H-1,4-diazepin-5-on-1-yl)-1,4-dihydro-4-oxoquinoline-3-carboxylic acid:

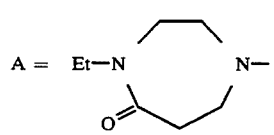

Yellow needles (CHCl₃-EtOH) m.p.: 276°–278° C.; IR (KBr): 3420, 3290, 1725, 1630 cm⁻¹; ¹H-NMR (CDCl₃) δ: 1.03–1.30(7H,m), 2.79–2.95(2H,m), 3.36–3.69(8H,m), 3.92(1H,m), 5.17(2H,brs), 8.65(1H,s).
Compound No. (1-8):
5-Amino-1-cyclopropyl-6,8-difluoro-7-(4-methyl-2,3,4,5,6,7-hexahydro-1H-1,4-diazepin-5-on-1-yl)-1,4-dihydro-4-oxoquinoline-3-carboxylic acid:

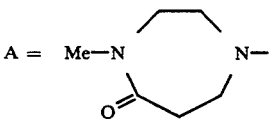

Yellow powder (CHCl₃-EtOH); m.p.: 281°–283° C.; IR (KBr): 3430, 3305, 1725, 1635 cm⁻¹; ¹H-NMR (CDCl₃) δ: 1.05–1.30(4H,m), 2.85–2.90(2H,m), 3.07(3H,s), 3.40–3.75(6H,m), 3.93(1H,m), 6.50(2H,brs), 8.66(1H,s).

Example 4

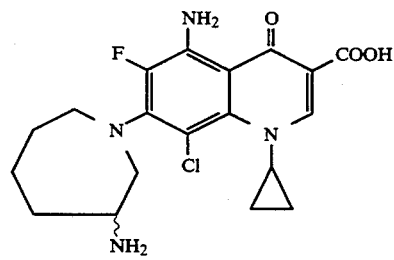

5-Amino-7-(3-amino-2,3,4,5,6,7-hexahydro-1H-azepin-1-yl)-8-chloro-1-cyclopropyl-6-fluoro-4-oxo-quinoline-3-carboxylic acid (Compound No. 1-9):

One hundred milligrams (0.32 mmol) of 5-amino-8-chloro-1-cyclopropyl-6,7-difluoro-4-oxoquinoline-3-carboxylic acid (2-2) and 114 mg (1.00 mmol) of DL-3-aminohexahydro-1H-azepin were suspended in 5 ml of acetonitrile, and the resultant suspension was heated under reflux for 5 hours. After allowing the suspension to cool, a precipitate was collected by filtration and recrystallized from acetonitrile to obtain 32 mg (yield: 25%) of the intended compound (1-9) according to the present invention.

Pale yellow powder (CH₃CN); m.p.: 145°–147° C. IR (KBr): 1627 cm⁻¹; ¹H-NMR (DMSO-d₆) δ: 0.88–1.20(4H,m), 1.40–1.90(6H,m), 2.80–3.30(5H,m), 4.15–4.40(1H,m), 4.70(2H,brs), 6.36(2H,brs), 8.65(1H,s).

Example 5

The following compounds (Compound Nos. 1-10 through 1-12) were obtained by reactions similar to Example 4.

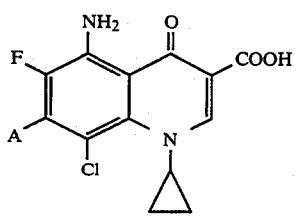

Compound No. (1-10):
5-Amino-8-chloro-1-cyclopropyl-6-fluoro-7-(2,3,4,5,6,7-hexahydro-1H-1,4-diazepin-5-on-1-yl)-4-oxo-quinoline-3-carboxylic acid:

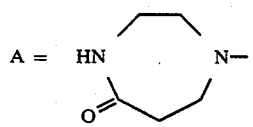

Yellow needles (CHCl$_3$-EtOH); m.p.: 265°–268° C. (decomposed) IR (KBr): 1715, 1650 1625 cm$^{-1}$; $^1$H-NMR (DMSO-d$_6$) δ: 0.80–1.25(4H,m), 2.55–2.70 (2H, m), 3.20–3.40(6H,m), 4.10–4.40(1H,m), 7.57(2H,brs), 8.67(1H,s).

Compound No. (1-11):
R-5-Amino-7-(3-amino-2,3,4,5,6,7-hexahydro-1H-azepin-1-yl)-8-chloro-1-cyclopropyl-6-fluoro-4-oxoquinoline-3carboxylic acid:

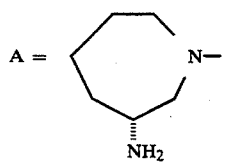

Pale yellow powder (CH$_3$CN); m.p.: 146°–149° C. IR (KBr): 1628 cm$^{-1}$; $^1$H-NMR (DMSO-d$_6$) δ: 0.80–1.20(4H,m), 1.40–1.90(6H,m), 2.60–3.30(5H,m), 4.10–4.40(1H,m), 4.70(2H,brs), 7.52(2H,brs), 8.65(1H,s).

Compound No. (1-12):
S-5-Amino-7-(3-amino-2,3,4,5,6,7-hexahydro-1H-azepin-1-yl)-8-chloro-1-cyclopropyl-6-fluoro-4-oxoquinoline-3-carboxylic acid:

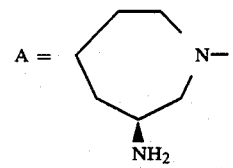

Pale yellow powder (CH$_3$CN); m.p.: 208°–211° C. (decomposed) IR (KBr): 1636 cm$^{-1}$; $^1$H NMR (DMSO-d$_6$) δ: 0.78–1.22(4H,M), 1.40–1.95(6H,m), 2.60–3.40(5H,m), 4.10–4.40(1H,m), 5.50(2H,brs), 7.54(2H,brs), 8.64(1H,s).

Test Example 1

Antibacterial test:

Antibacterial activities against microorganisms shown in Tables 1–3 were measured according to the MIC measurement method of The Japan Chemotherapeutic Association. Sparfloxacin was used as a control agent. The results are shown in Tables 1–3.

Medium: Mueller Hinton Medium

Sample dilution:

A 1,000 micrograms/ml solution in 25% dimethylsulfoxide was prepared. A series of solutions with various concentrations (100 micrograms to 0.006 micrograms) were prepared by successively diluting the solution with sterilized water by a factor of ½.

Amount of inoculated bacteria: 10$^6$/ml

Cultivation conditions: 37° C., 48 hours

Determination: After 24 hours.

TABLE 1

| | MIC (μg/ml) | | | |
| Strain tested | Compound No. (1-2) | Compound No. (1-8) | Compound No. (1-10) | Sparfloxacin |
| --- | --- | --- | --- | --- |
| Gram-positive bacteria | | | | |
| 1. *Bacillus subtilis* ATCC 6633 | 0.006 | 0.006 | 0.012 | 0.024 |
| 2. *Staphylococcus aureus* FDA 209P | 0.012 | 0.006 | 0.012 | 0.024 |
| 3. *Staphylococcus aureus* Terashima | 0.05 | 0.05 | 0.10 | 0.10 |
| 4. *Staphylococcus aureus* Smith | 0.006 | 0.012 | 0.006 | 0.05 |
| 5. *Staphylococcus epidermidis* ATCC 12228 | 0.05 | 0.10 | 0.024 | 0.20 |
| 6. *Sarcina lutea* ATCC 9341 | 0.39 | 0.39 | 0.20 | 1.56 |
| 7. *Streptococcus faecalis* IFO 12964 | 0.20 | 0.20 | 0.20 | 0.39 |
| 8. *Micrococcus lysodeikticus* IFO 3333 | 0.05 | 0.10 | 0.05 | 0.39 |

TABLE 2

| | MIC (μg/ml) | | | |
| Strain tested | Compound No. (1-2) | Compound No. (1-8) | Compound No. (1-10) | Sparfloxacin |
| --- | --- | --- | --- | --- |
| Gram-negative bacteria | | | | |
| 9. *Escherichia coli* O-1 | 0.05 | 0.10 | 0.10 | 0.012 |
| 10. *Escherichia coli* K-12 | 0.05 | 0.10 | 0.10 | 0.012 |
| 11. *Salmonella typhi* TD | 0.05 | 0.10 | 0.10 | 0.006 |
| 12. *Shigella flexneri* 2b | 0.006 | 0.006 | 0.006 | 0.006 |
| 13. *Pseudomonas aeruginosa* IFO 13736 | 3.13 | 3.13 | 6.25 | 0.78 |
| 14. *Pseudomonas aeruginosa* P2 | 6.25 | 12.5 | 12.5 | 1.56 |
| 15. *Pseudomonas aeruginosa* IFO 12582 | 3.13 | 6.25 | 3.13 | 1.56 |
| 16. *Klebsiella pneumoniae* ATCC 10031 | 0.006 | 0.006 | 0.05 | 0.006 |
| 17. *Klebsiella pneumoniae* IFO 13541 | 0.05 | 0.10 | 0.10 | 0.012 |

TABLE 2-continued

| | MIC (μg/ml) | | | |
|---|---|---|---|---|
| Strain tested | Compound No. (1-2) | Compound No. (1-8) | Compound No. (1-10) | Spafloxacin |
| 18. *Proteus vulgaris* OXK | 0.05 | 0.10 | 0.20 | 0.05 |
| 19. *Proteus rettgeri* | 0.39 | 0.39 | 0.78 | 0.10 |
| 20. *Serratia marcescens* NHL | 0.78 | 1.56 | 1.56 | 0.20 |

TABLE 3

| | MIC (μg/ml) | | | |
|---|---|---|---|---|
| Strain tested | Compound No. (1-2) | Compound No. (1-8) | Compound No. (1-10) | Spafloxacin |
| Methicillin-resistant *Staphylococcus aureus* (MRSA), Gram-positive bacteria | | | | |
| 21. M. R. *Staphylococcus aureus* 395 | 0.05 | 0.05 | 0.024 | 0.10 |
| 22. M. R. *Staphylococcus aureus* 415 | 0.024 | 0.024 | 0.012 | 0.05 |
| 23. M. R. *Staphylococcus aureus* 419 | 0.024 | 0.024 | 0.024 | 0.05 |
| 24. M. R. *Staphylococcus aureus* 420 | 0.05 | 0.05 | 0.012 | 0.10 |
| 25. M. R. *Staphylococcus aureus* 421 | 0.012 | 0.024 | 0.024 | 0.05 |

INDUSTRIAL APPLICABILITY

The 5-aminoquinolone carboxylic acid derivatives according to the present invention exhibit strong antibacterial activities against Gram-positive bacteria including tolerant bacterial while retaining good antibacterial activities on Gramnegative bacteria, and are satisfactorily absorbed in a living body, so that they are useful in prevention of and treatment for a variety of clinical infective diseases.

We claim:

1. A 5-aminoquinolone carboxylic acid derivative represented by the following general formula (1):

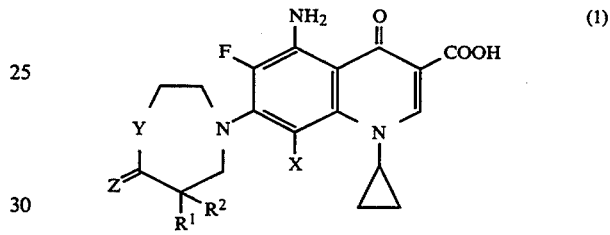

wherein $R^1$ means a hydrogen atom, am amino group, a linear or branched alkyl group having 1-5 carbon atoms and an alkylamino group containing a linear or branched alkyl group having 1-5 carbon atoms, $R^2$ denotes a hydrogen atom or a linear or branched alkyl group having 1-5 carbon atoms, X stands for a halogen atom, Y means $CH_2$, NH, $CHR^3$, $NR^3$ ($R^3$ denoting a linear or branched alkyl group having 1-5 carbon atoms) or an oxygen atom, and Z stands for an oxygen atom, or a salt thereof.

2. An antibacterial agent containing, as an active ingredient, the 5-aminoquinolone carboxylic acid derivative or salt thereof as set forth in claim 1.

* * * * *